(12) United States Patent
Volyanskyy et al.

(10) Patent No.: US 11,640,852 B2
(45) Date of Patent: May 2, 2023

(54) SYSTEM FOR LABORATORY VALUES AUTOMATED ANALYSIS AND RISK NOTIFICATION IN INTENSIVE CARE UNIT

(71) Applicant: KONINKLIJKE PHILIPS N. V., Eindhoven (NL)

(72) Inventors: Kostyantyn Volyanskyy, Larchmont, NY (US); Minnan Xu, Cambridge, MA (US); Larry James Eshelman, Ossining, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 690 days.

(21) Appl. No.: 15/564,110

(22) PCT Filed: Mar. 17, 2016

(86) PCT No.: PCT/IB2016/051494
§ 371 (c)(1),
(2) Date: Oct. 3, 2017

(87) PCT Pub. No.: WO2016/162767
PCT Pub. Date: Oct. 13, 2016

(65) Prior Publication Data
US 2018/0082042 A1    Mar. 22, 2018

Related U.S. Application Data

(60) Provisional application No. 62/144,374, filed on Apr. 8, 2015.

(51) Int. Cl.
*G16H 10/40*    (2018.01)
*G16H 50/30*    (2018.01)
*G16H 10/60*    (2018.01)

(52) U.S. Cl.
CPC ............ *G16H 10/40* (2018.01); *G16H 10/60* (2018.01); *G16H 50/30* (2018.01)

(58) Field of Classification Search
CPC ...... G16H 10/60; G16H 50/30; G06F 19/328; G06F 19/3418
See application file for complete search history.

(56) References Cited

U.S. PATENT DOCUMENTS 7,899,764 B2 *  3/2011 Martin ................... G06Q 50/24
                                                706/12
8,473,306 B2 *  6/2013 Seely ..................... G16H 10/60
                                                705/2
(Continued)

FOREIGN PATENT DOCUMENTS

EP      2365456 A2    9/2011
WO   2007011412 A2    1/2007
(Continued)

OTHER PUBLICATIONS

José M. Carmona-Cejudo et al., DB4US:A Decision Support System for Laboratory Information Management, 1(2):e16 Interact J Med Res 1 (Year: 2012).*
(Continued)

*Primary Examiner* — Evangeline Barr
*Assistant Examiner* — Jordan L Jackson (57) ABSTRACT

In a risk level assessment method for a plurality of clinical conditions as follows, a set of laboratory test results (32) are stored with time stamps for a patient, including at least one hematology test result and at least one arterial blood gas (ABG) test result. For each clinical condition, a risk level is determined for the clinical condition based on a clinical condition-specific sub-set of the stored set of laboratory test
(Continued)

results. This determination is made conditional on the stored clinical condition-specific sub-set of laboratory test results being sufficient to determine the risk level. A time stamp is assigned to each determined risk level based on the time stamps for the laboratory test results of the clinical condition-specific sub-set of laboratory test results. A display device (44, 46) displays the determined risk level and the assigned time stamp for each clinical condition whose determined risk level satisfies a display criterion.

20 Claims, 4 Drawing Sheets

(56) References Cited

U.S. PATENT DOCUMENTS

| | | | | |
|---|---|---|---|---|
| 10,299,689 | B2* | 5/2019 | Ong | A61B 5/14552 |
| 10,489,904 | B2* | 11/2019 | Barnes | G06K 9/629 |
| 2007/0192134 | A1* | 8/2007 | Littenberg | G16H 70/20 |
| | | | | 705/2 |
| 2009/0125328 | A1 | 5/2009 | Nevins | |
| 2010/0042429 | A1 | 2/2010 | Dixit | |
| 2011/0199214 | A1* | 8/2011 | Gawlick | A61B 5/0008 |
| | | | | 340/573.1 |
| 2011/0225114 | A1 | 9/2011 | Gotthardt | |
| 2012/0209082 | A1* | 8/2012 | Al-Ali | A61B 5/02055 |
| | | | | 600/300 |
| 2013/0262357 | A1 | 10/2013 | Amarasingham et al. | |
| 2014/0074509 | A1 | 3/2014 | Amarasingham et al. | |
| 2014/0257122 | A1* | 9/2014 | Ong | A61B 5/02405 |
| | | | | 600/515 |
| 2015/0011844 | A1* | 1/2015 | Paradis | G16B 40/30 |
| | | | | 600/301 |
| 2015/0025329 | A1* | 1/2015 | Amarasingham | G16H 40/67 |
| | | | | 600/301 |
| 2015/0088531 | A1* | 3/2015 | Comanita | G06Q 50/22 |
| | | | | 705/2 |

FOREIGN PATENT DOCUMENTS

| | | |
|---|---|---|
| WO | 2014160777 A1 | 10/2014 |
| WO | 2014201515 A1 | 12/2014 |
| WO | 2015023674 A1 | 2/2015 |

OTHER PUBLICATIONS

Chih-Lin Chi, Medical decision support systems based on machine learning</i>, Doctor of Philosophy Thesis, University of Iowa (Year: 2009).*

Fleur T. Tehrani, A New Decision Support System for Mechanical Ventilation, Conference proceedings : Annual International Conference of the IEEE Engineering in Medicine and Biology Society, IEEE Engineering in Medicine and Biology Society.Conference 3569-72 (Year: 2007).*

Chih-Lin Chi, Medical decision support systems based on machine learning, Doctor of Philosophy Thesis, University of Iowa (Year: 2009).*

Singh et al., Incorporating temporal HER data in predictive models for risk stratification of renal function deterioration, 53 J. of Biomedical Informatics 220-228 (Nov. 15, 2014) (Year: 2014).*

Nancy Epstein, Morbidity and mortality conferences: Their educational role and why we should be there, 3(Suppl 5) Surgical Neurology Int S377-S388 (Nov. 26, 2012) (Year: 2012).*

Electronic Clinical Quality Measure Logic and Implementation Guidance and Technical Release Notes, Centers for Medicare & Medicaid Services Office of the National Coordinator for Health Information Technology v1.7 (Apr. 1, 2014) (Year: 2014).*

\* cited by examiner

SYSTEM FOR LABORATORY VALUES AUTOMATED ANALYSIS AND RISK NOTIFICATION IN INTENSIVE CARE UNIT

CROSS-REFERENCE TO PRIOR APPLICATIONS

This application is the U.S. National Phase application under 35 U.S.C. § 371 of International Application No. PCT/M2016/051494, filed on Mar. 17, 2016, which claims the benefit of U.S. Provisional Application Ser. No. 62/144,374, filed Apr. 8, 2015. These applications are hereby incorporated by reference herein, for all purposes.

FIELD

The following relates generally to the critical medical care arts, medical laboratory testing arts, and related arts.

BACKGROUND

Laboratory test results are performed on tissue samples (e.g. blood, urine, et cetera) to generate clinically useful results such as blood gas levels ($PaO_2$, $PaCO_2$, ... ), a complete blood count panel (white cells, red cells, hemoglobin, hematocrit, platelets, ... ), measurements of various electrolytes, creatinine, kinase isoenzymes, or so forth. In an ICU setting, specimens are drawn from the patient at intervals and tested, and the results are written on the patient chart. More recently, electronic data recordation and transfer has been standardized, e.g. using the HL7® ANSI-accredited exchange standard, so that such data can be automatically recorded in the patient's Electronic Health or Medical Record (EHR or EMR) and electronically distributed to the doctor, nurse, or other authorized persons or entities (in accord with HIPAA or other applicable privacy standards).

However, these improvements in data recordation and exchange have not necessarily translated into more effective leveraging of laboratory tests for patient monitoring/treatment, and numerous limitations remain. Physicians have a tendency to consider individual laboratory results in isolation, and may fail to recognize clinically probative patterns in diverse laboratory results, especially if the clinically probative pattern pertains to a clinical condition that is outside of a physician's area of specialization. This tendency is amplified by the discrete nature of laboratory tests: different laboratory results, even if electronically recorded and distributed, generally become available to the physician at different times due to discrete/semi-manual specimen collection and processing. A Physician attends to many patients, and laboratory tests are usually outsourced to a testing laboratory, which in some cases may not even be located in the hospital (e.g., an outside contract laboratory). Such factors may make it difficult for a physician to collate different laboratory test results into a useful pattern. Still further, if a pattern is identified which is made up of laboratory test results acquired over an extended period of time, it may be difficult to assign a meaningful date to a medical conclusion drawn from the pattern.

The following discloses a new and improved systems and methods that address the above referenced issues, and others.

SUMMARY

In one disclosed aspect, a computer is programmed to perform a risk level assessment method for a plurality of clinical conditions as follows. A set of laboratory test results with time stamps for a patient including at least one hematology test result and at least one arterial blood gas (ABG) test result are stored on a non-transitory storage medium. For each clinical condition, a risk level is determined for the clinical condition based on a clinical condition-specific sub-set of the stored set of laboratory test results. This determination is made conditional on the stored clinical condition-specific sub-set of laboratory test results being sufficient to determine the risk level. A time stamp is assigned to each determined risk level based on the time stamps for the laboratory test results of the clinical condition-specific sub-set of laboratory test results. A display device is caused to display the determined risk level and the assigned time stamp for each clinical condition whose determined risk level satisfies a display criterion.

In another disclosed aspect, a non-transitory storage medium stores instructions readable and executable by an electronic data processing device to perform a risk level assessment method for a plurality of clinical conditions. The risk level assessment method includes the following operations. For each clinical condition, it is determined whether sufficient laboratory test results are stored in a laboratory test results data structure to perform risk level assessment for the clinical condition. If sufficient laboratory test results are available, a risk level is determined for the clinical condition based on a clinical condition-specific sub-set of the set of laboratory test results, and a time stamp is assigned to the determined risk level based on the time stamps for the laboratory test results of the sub-set of laboratory test results. A display device is caused to display the determined risk levels of clinical conditions for which the risk level satisfies a display criterion and to display the assigned time stamp for each displayed risk level.

In another disclosed aspect, a method comprises: storing a set of laboratory test results including at least one hematology test result and at least one arterial blood gas (ABG) test result using a computer-readable non-transitory storage medium; determining a risk level for a clinical condition based on a clinical condition-specific sub-set of the set of laboratory test results; assigning a time stamp to the determined risk level based on the time stamps for the laboratory test results of the sub-set of laboratory test results; and displaying, on a display device, the determined risk level and the assigned time stamp.

One advantage resides in providing automated detection of clinically probative patterns in diverse laboratory test results.

Another advantage resides in providing automated time stamping for a clinically probative pattern of laboratory test results.

Another advantage resides in providing automatic identification and notification of quantitative risks of various clinical conditions based on combinations of laboratory test results.

Another advantage resides in providing guidance as to scheduling of laboratory tests to provide synergistic information about the patient.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
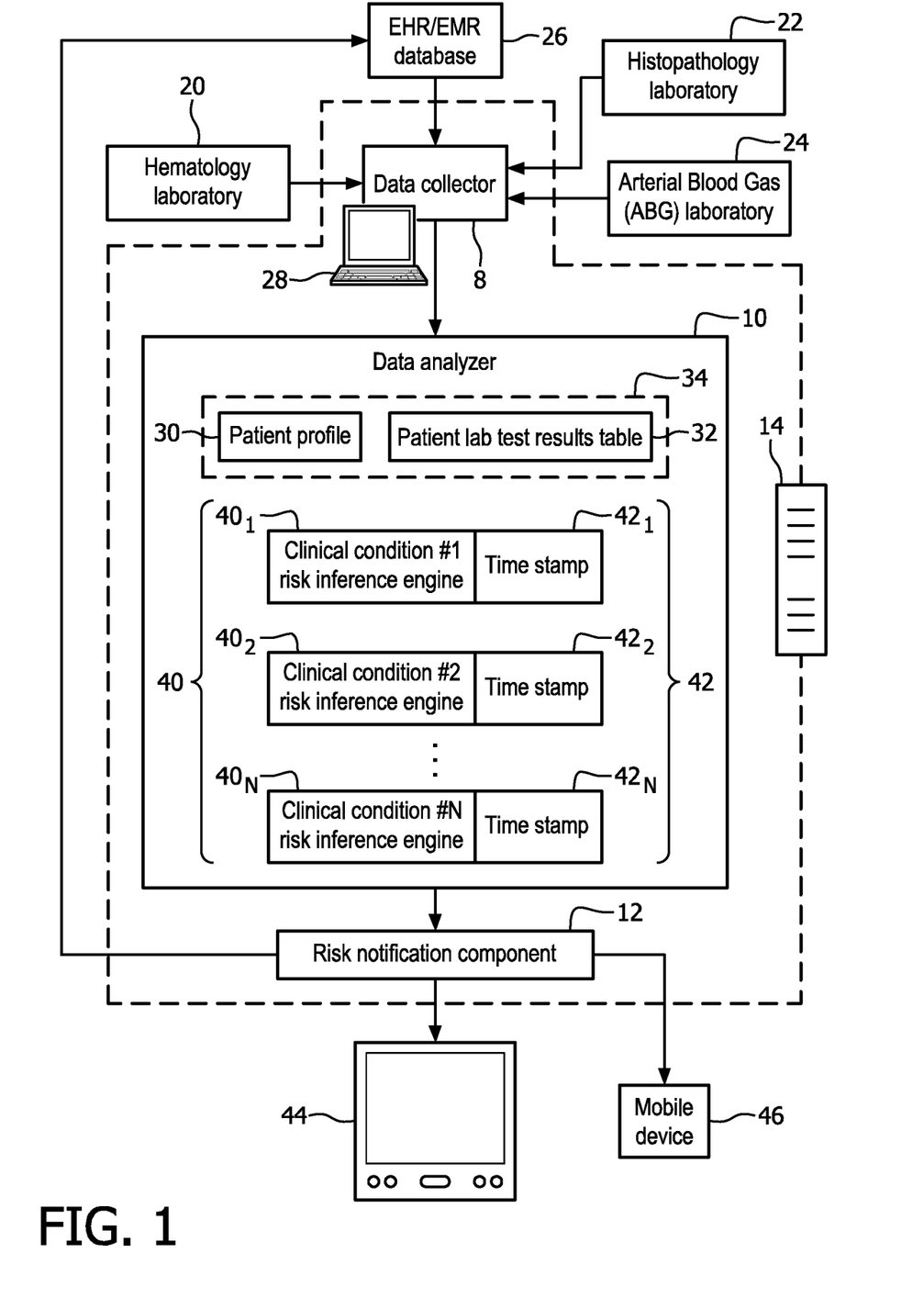
FIG. 1 diagrammatically illustrates a system for automatic identification and notification of quantitative risks of various clinical conditions based on combinations of laboratory test results.

With reference to FIG. 1, a system is disclosed for automatic identification and notification of quantitative risks pertaining to various clinical conditions based on combinations of laboratory test results. The system includes three main components: a data collector 8, a data analyzer 10, and a risk notification component 12. These components 8, 10, 12 are suitably implemented on an illustrative server computer 14 or other electronic data processing device (e.g. desktop computer, electronic patient monitor device, or so forth; or various aggregations of devices, e.g. a cloud computing network, server cluster, or so forth). It will also be appreciated that the disclosed approaches for automatic identification and notification of quantitative risks pertaining to various clinical conditions based on combinations of laboratory test results may also be embodied as a non-transitory storage medium storing instructions readable and executable by the computer 14 or by another electronic data processing device to perform the disclosed methods. The non-transitory storage medium may, by way of illustration, include: a hard disk drive or other magnetic storage medium; an optical disk or other optical storage medium; a flash memory or other electronic storage medium; various combinations thereof; and so forth.

The data collector 8 is operatively connected with various data sources, such as various medical laboratories, diagrammatically indicated in FIG. 1 by an illustrative hematology laboratory 20, an illustrative histopathology laboratory 22, and an illustrative arterial blood gas (ABG) laboratory 24. The hematology laboratory 20 provides laboratory test results such as a complete blood count panel (white cells, red cells, hemoglobin, hematocrit, platelets, . . . ) or portions thereof as requested by the patient's physician, and blood serum values such as measurements of various electrolytes, creatinine, kinase isoenzymes, albumin, bilirubin, ammonia, alkaline phosphatase, lactic acid, glucose, cholesterol, iron, or so forth, in the blood. The histopathology laboratory 22 performs microscopic inspection of extracted tissue samples as requested by the physician. The ABG laboratory 24 measures various blood gas levels ($PaO_2$, $PaCO_2$, pH, $HCO_3$, . . . ) in an arterial blood sample. It will be appreciated that fewer, additional, and/or other laboratories may provide laboratory test results to the data collector 8, and moreover the illustrative laboratories may be variously combined, e.g. the hematology laboratory may also perform ABG analysis. The data collector 8 is also operatively connected with an Electronic Health (or Medical) Record (EHR/EMR) 26 or other patient data source in order to obtain patient data such as demographic data (age, sex, ethnicity, et cetera), chronic health conditions such as a heart condition or Chronic Obstructive Pulmonary Disorder (COPD), or other medical history information (e.g. information on any recent surgery), patient habits (smoker or non-smoker, et cetera), current medications, or so forth. Laboratory test result data and patient data may be delivered to the data collector 8 automatically, for example via an HL7® ANSI-accredited exchange standard-compliant electronic network for patient data recordation and transfer provided by the hospital or other medical setting, and optionally also connected with contract laboratories if such are employed by the hospital. Additionally or alternatively, some or all laboratory test results and/or some or all patient data may be entered manually using an electronic data entry terminal or computer 28.

Each laboratory test result collected by the data collector 8 is time stamped appropriately, usually using a time stamp assigned to the test result by the laboratory 20, 22, 24 that performed the laboratory test. For example, the time stamp for a laboratory test result obtained from an extracted blood or tissue sample may be appropriately set to the date/time that the tested blood or tissue sample was extracted. The term "time stamp" as used herein includes any chosen temporal designation, e.g. a time stamp may specify the calendar date of the test result, or may specify more particularly (i.e. with greater temporal resolution) both a calendar date and time-of-day of the test result (with various optional specifications, e.g. with or without the seconds, and/or with a time zone offset, or so forth). Patient data may also be assigned a time stamp as appropriate.

The data analyzer 10 performs analysis, such as probative pattern detection, on the laboratory test results in light of any relevant patient data. To this end, the data analyzer maintains a patient profile 30 (also referred to herein as a "P1-profile") which is a table or other data structure containing patient data (e.g. demographic and clinical information such as age, gender, medical history, current diagnosis, medications, and so forth). The data analyzer also maintains a patient laboratory test results table 32 (also referred to herein as a "P2-profile") which is a table or other data structure containing laboratory tests results, optionally organized by test class or other organizational criteria. The patient profile 30 and the patient laboratory test results table or other data structure 32 are suitably stored using a non-transitory storage medium 34 which may, by way of illustration, include: a hard disk drive or other magnetic storage medium; an optical disk or other optical storage medium; a flash memory or other electronic storage medium; various combinations thereof; and so forth.

The data analyzer 10 may optionally perform certain "per-test" analyses (not illustrated). For example, the current value of each laboratory test result may be compared against a normal range for that test result, and a preliminary risk level assigned for a clinical condition based on P1-profile data. For example, $PaO_2$ may be compared against a normal range for $PaO_2$ where the "normal range" depends on various patient data such as age and whether the patient has COPD. Along with current time values the test results table 32 may record dynamic information such as the change of each lab test result when compared with the previous test run, and positive and negative trends identified for a given time-window.

The data analyzer also processes the laboratory test results stored in the table 32 to detect patterns of laboratory test results that may be probative of a clinical condition such as a deteriorating organ or organ system or the onset of a serious medical condition such as sepsis, hypoxia, or so forth. To this end, the data analyzer 10 implements various clinical condition risk inference engines 40, designated in illustrative FIG. 1 as clinical condition #1 risk inference engine $40_1$, clinical condition #2 risk inference engine $40_2$, and so on through clinical condition #N risk inference engine $40_N$. (The number of different clinical condition risk inference engines is designated here as "N" without loss of generality). Each risk inference engine 40 may be implemented as an empirically trained classifier, a codified inference rule (or set of rules), a mathematical model of organ function, or other inference algorithm which is applied to a set of patient laboratory test results (which set is a sub-set of the test results contained in the table 32) along with any relevant patient data from the table 30 assign a risk level for the corresponding clinical condition. Each computed risk level is assigned a corresponding time stamp 42 based on the time stamps of the laboratory test results of the set of test results upon which the risk inference engine operates. Thus, the risk level for clinical condition #1 has a corresponding time stamp $42_1$, the risk level for clinical condition #2 has a corresponding time stamp $42_2$, and so on through the risk level for clinical condition #N which has corresponding time stamp $42_N$.

In one approach, a clinical condition risk inference engine 40 is constructed empirically as follows. Various sub-groups of laboratory values and their trends (e.g., {Albumin, Bicarbonate, pH, Lactic acid, Hg}, {Creatinine, BUN, BUN/Creatinine}, {Glucose, WBC}) are identified as probable indicators of the clinical condition based on information drawn from the medical literature and/or identified in consultation with medical experts. These sub-groups of medical test results may optionally be combined with other possibly relevant patient data, again based on the medical literature and/or expert knowledge. The resulting set of parameters form a set of features on which to train the clinical condition risk inference engine, which may for example be implemented as a machine learned linear regression model, logistic regression model, neural network, or other model or parameterized inference algorithm. Training data are drawn from labeled past patient examples (both positive examples of patients labeled as having had the clinical condition whose risk is to be inferred, and negative examples labeled as not having had the condition). An ensemble learning algorithm or other machine learning technique appropriate for learning the weights or other parameters of the model or inference algorithm is then applied to train the clinical condition risk inference engine 40 to generate a risk score given an input data set of values for the parameters such that the clinical condition inference engine 40 effectively distinguishes between the positive and negative examples of the training set. The summed or otherwise aggregated error between the labels of the training data and the inference engine output for the training data is minimized during the training. The machine learning may optionally also include a feature reduction component (incorporated into the learning or performed prior to the learning) to identify and discard features (i.e. laboratory tests) that are empirically found to have minimal impact on the machine learned clinical condition risk inference, so as to provide a smaller probative set of test results for the risk assessment performed by the clinical condition risk inference engine 40.

An advantage of the foregoing machine learning approach is that it provides a discovery mechanism for identifying and refining probative patterns of laboratory test results for use in assessing risk of (onset of) a particular clinical condition. On the other hand, if a pattern of laboratory test results is known to be indicative of (onset of) a particular clinical condition a priori, for example because a set of rules has been published in the medical literature via which a physician may infer the clinical condition is present or incipient, then this a priori-known set of rules can be codified to construct the inference engine. As yet another example, an inference engine can be constructed using a mathematical model of organ function that is suitably characterized by results of a set of laboratory tests. Various hybrids are also contemplated, e.g. a semi-empirical model of the organ function having weights or other parameters that are optimized by machine learning.

The output of each clinical condition risk inference engine $40_1, \ldots, 40_N$ is a risk level for the respective clinical condition #1, . . . , #N. These risk levels are input from the data analyzer 10 to the risk notification component 12, which outputs information pertaining to the risks to a physician, nurse, or other medical personnel via a suitable user interfacing device such as a patient monitor 44, a wireless mobile device 46 such as a cellular telephone (cell phone), medical pager, or the like running an application program ("app") interfacing with the computer 14 (and more particularly with the risk notification component 12) via a 3G, WiFi, or other wireless network, a nurses station computer, or so forth. In some illustrative embodiments described herein, the risk notification component 12 performs ranking, filtering, or other processing of the risk levels so that only the most critical risk(s) (if any) are reported to medical personnel. Optionally, the risk notification component 12 logs all risk values in patient record for the patient being monitored in the EHR/EMR database 26.

In applying any of the clinical condition risk inference engines $40_1, \ldots, 40_N$ two difficulties may arise. First, some of the input patient data for assessing risk of the clinical condition may be missing, either because a laboratory test was not (or has not yet been) performed or because the available test result is "stale", i.e. too old to be relied upon. Second, it is not readily apparent what time stamp 42 should be assigned to the inferred risk level when the various input laboratory test results have different individual time stamps. This latter difficulty could lead to misinterpretation of the risk level if, for example, the physician assumes the risk level is current as of the most recent laboratory test ordered by the physician to assess the clinical condition when in fact the clinical condition risk inference engine relied upon a set of input data that also includes laboratory test results that are significantly older than this last-obtained test result.

Figure 2:
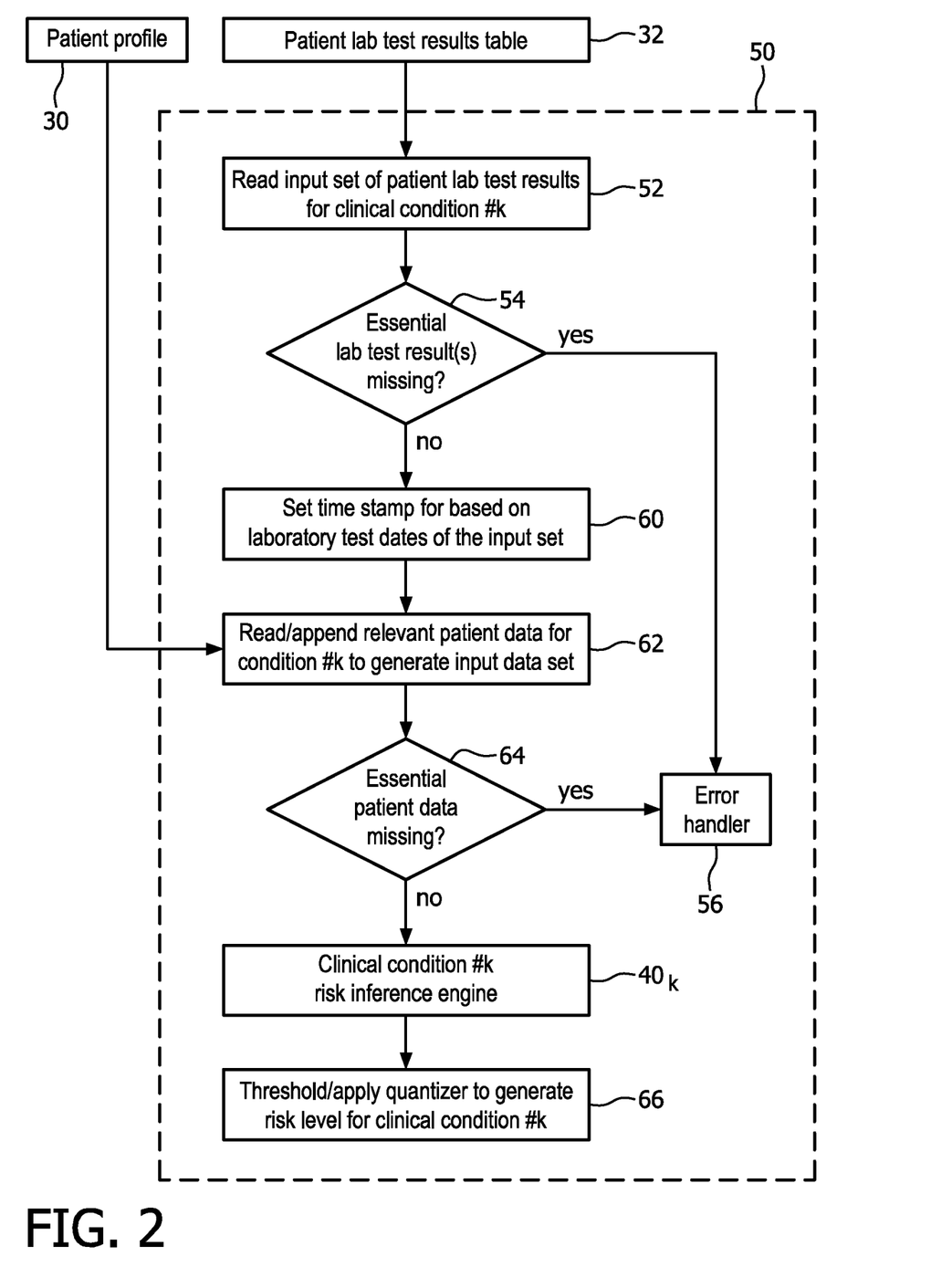
FIG. 2 diagrammatically illustrates processing suitably performed by one of the clinical condition risk inference engines of the system of FIG. 1.

With reference to FIG. 2, an illustrative inference process 50 suitably performed by the data analyzer 10 in applying one of the clinical condition risk inference engines 40 is described. In FIG. 2, reference is made to a clinical condition #k, where without loss of generality #k denotes one of the clinical conditions #1, . . . , #N and is assessed using the clinical condition risk inference engine 40 k which is one of the clinical condition risk inference engines 40 of FIG. 1. In an operation 52, an input set of patient laboratory test results for assessing clinical condition #k is acquired from the patient laboratory test results table 32. This set of laboratory test results is a sub-set of the complete table of test results 32, and was defined during the training of the clinical condition risk inference engine 40 k (or, alternatively was defined by the set of codified literature rules, mathematical organ model, or other source from which the clinical condition risk inference engine 40 k was generated). In an operation 54, it is determined whether the set of patient laboratory test results read from the patient laboratory test results table 32 is missing any essential laboratory test results. By "essential" it is meant that the clinical condition risk inference engine 40 k is not considered to produce a reliable result without that essential laboratory test result. Some laboratory test results, while being used by the clinical condition risk inference engine 40 k, may be considered non-essential because they have a relatively weak impact on the risk level output by the clinical condition risk inference engine 40 k—in such cases, the missing non-essential test result can be filled in with a default "typical" value for the laboratory test. In some cases, the clinical condition risk inference engine 40 k may be constructed to operate either with or without the non-essential test result (for example, by being constructed to employ a default value if the test result is unavailable, or by applying a different trained classifier that does not rely upon the non-essential test result if it is unavailable). In determining whether an essential laboratory test result is missing, the operation 54 may take into account the time stamp of the test result, so that for example a test result that is available but is too old (i.e. stale) is deemed to be missing as the stale essential test result cannot be relied upon in applying the clinical condition risk inference engine 40 k.

If the operation 54 determines that a laboratory test result that is essential for applying the clinical condition risk inference engine $40_k$ is missing, then flow passes to an error handler 56 which takes remedial action. This remedial action, at a minimum, preferably includes providing some indication that the risk level for clinical condition #k is not available. This may be done by setting a suitable binary flag associated with clinical condition #k to indicate unavailability, and/or by setting the time stamp for the risk level for clinical condition #k to a value such as −1 so as to indicate unavailability, or so forth. The error handler 56 may optionally also provide medical personnel with a recommendation (e.g. displayed on the display device 44, 46) that the laboratory test that produces the missing laboratory test result should be performed in order to assess the risk for clinical condition #k. If the test has been performed but is stale, the displayed message may indicate the existing test result is stale and should not be relied upon.

Figure 3:
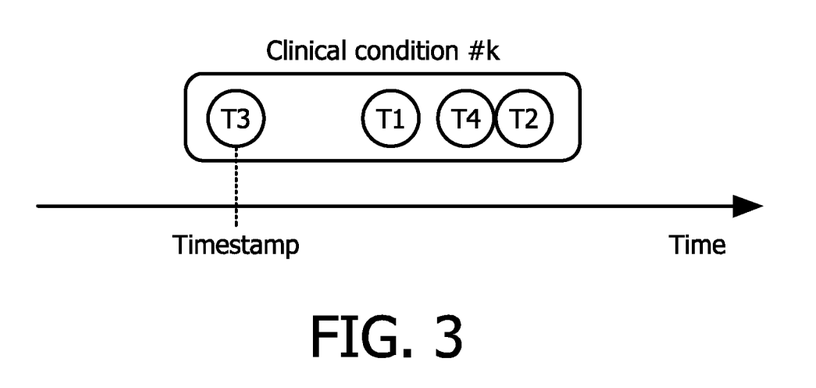
FIGS. 3 and 4 diagrammatically show two illustrative approaches for assigning a time stamp to an clinical condition risk assessed based on four laboratory test results respectively designated "T1", "T2", "T3", and "T4".
Figure 4:
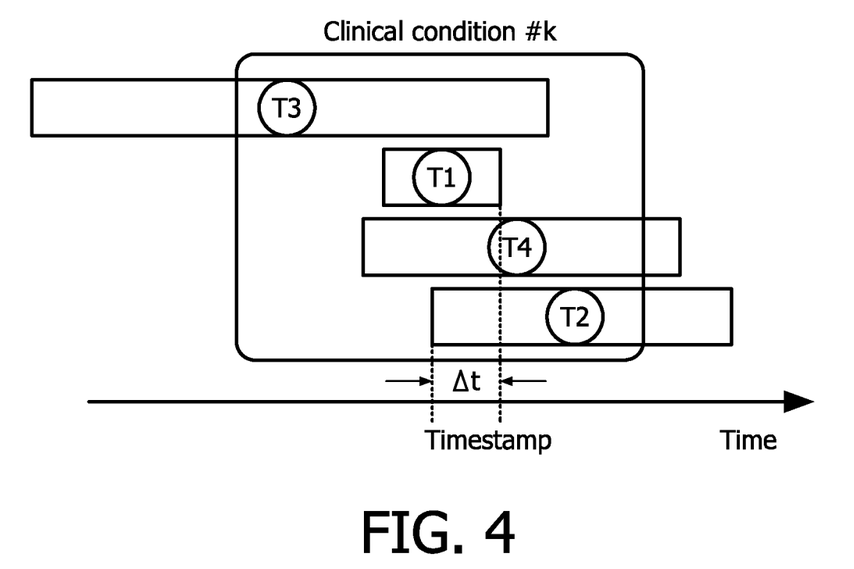

With continuing reference to FIG. 2 and with brief reference to FIGS. 3 and 4, if all essential laboratory test results are determined to be available in the operation 54, then flow passes to an operation 60 in which the time stamp for the risk level associated with condition #k is determined based on the time stamps of the laboratory test results of the input set of test results retrieved in the read operation 52. Various approaches can be used to choose the time stamp for the risk level for clinical condition #k, two of which are diagrammatically shown in respective FIGS. 3 and 4. The approach diagrammatically shown in FIG. 3 assigns the risk level the time stamp of the oldest time stamp of any of the input test results. Thus, in illustrative FIG. 3 the clinical condition risk inference engine $40_k$ uses four laboratory test results designated as "T1", "T2", "T3", and "T4", which were acquired (i.e. have time stamps) in the order "T3", "T1", "T4", "T2" as shown in FIG. 3. In the approach of FIG. 3, the time stamp for the risk level of clinical condition #k is then assigned the time stamp of the oldest laboratory test result, here being the time stamp for test result "T3".

The approach of FIG. 3 does not take into account the time frame over which a laboratory test result may be relied upon. For example, if the physiological feature measured by a test is slowly varying, then the test result may be reliable for a significant time period after the test is performed, and similarly it is reasonable to assume that the test result is representative over comparable time period before the test was performed. By contrast, if the physiological feature measured by the test tends to fluctuate rapidly over time, then the window over which the test result is reasonably relied upon is substantially shorter. The illustrative approach of FIG. 4 applies a time window for each test result, as diagrammatically indicated by a box-type range associated with each of "T1", "T2", "T3", "T4". Since the illustrative risk level for clinical condition #k relies upon the combination of "T1", "T2", "T3", "T4", the overlap or intersection of all four time windows for "T1", "T2", "T3", "T4", i.e. $\Delta t = W(T1) \cap W(T2) \cap W(T3) \cap W(T4)$ where $W(\ldots)$ is the time window and "$\cap$" is the binary intersection operator. The time stamp for the risk level computed for clinical condition #k is then suitably set to the most recent end of overlap time interval $\Delta t$. Note that if all time windows extend to the present time, then the time stamp for the risk level could reasonably be set to the present time so as to indicate the risk level is current. On the other hand, if there is no mutual overlap between all windows $W(T1)$, $W(T2)$, $W(T3)$, and $W(T4)$ (that is, $\Delta t = 0$) then the risk level cannot be reliably computed, and flow may suitably transfer to the error handler 56 to (for example) recommend ordering one or more new laboratory tests.

With continuing reference to FIG. 2, in read operation 62 any relevant patient data (i.e. patient data used by the clinical condition #k risk inference engine $40_k$) is read from the patient profile 30. At a decision operation 64, it is determined whether any essential patient data are missing. "Essential" patient data is defined analogously to "essential" laboratory test results—essential patient data are patient data without which a reliable risk level for clinical condition #k cannot be estimated using the clinical condition #k risk inference engine $40_k$. If a missing patient datum is non-essential, then the clinical condition #k risk inference engine $40_k$ can still be applied, for example by inserting a default value for the missing patient datum. If at the decision operation 64 any essential patient data are identified as missing, then the error handler 56 is invoked to take remedial action, such as requesting that the missing patient data be entered into the EHR/EMR 26 in order to be transferred to the data collector 8 (or entered directly into the data collector 8).

If at the decision 64 it is determined that all essential patient data are available (and since earlier decision 54 determined that all essential laboratory test results are available), then flow passes to the clinical condition #k risk inference engine $40_k$ where the risk score is computed for clinical condition #k, with the time stamp assigned in operation 60. Optionally, further processing 66 is performed, for example to apply a threshold or quantization to the risk score to generate the risk level as a more readily perceived risk assessment. For example, a threshold may be applied so that the final output is: "significant risk of clinical condition #k" or "no significant risk of clinical condition #k". In another example, a quantizer is applied to the score to form the final output as one of a series of levels, such as: "red"="high risk of clinical condition #k", "yellow"="moderate risk of clinical condition #k", or "green"="low risk of clinical condition #k".

The illustrative process flow of FIG. 2 and illustrative risk level time stamping algorithms of FIGS. 3 and 4 are to be understood as non-limiting examples. The process flow may be variously adjusted, for example the time stamp may be assigned after computing the risk level, patient data may be read before test results, the time stamp may be set to the middle of the time interval $\Delta t$ rather than its end, or as another illustrative example the time stamp for the risk level may be set to the time stamp of one particular "most critical" test result, or so forth.

Figure 5:
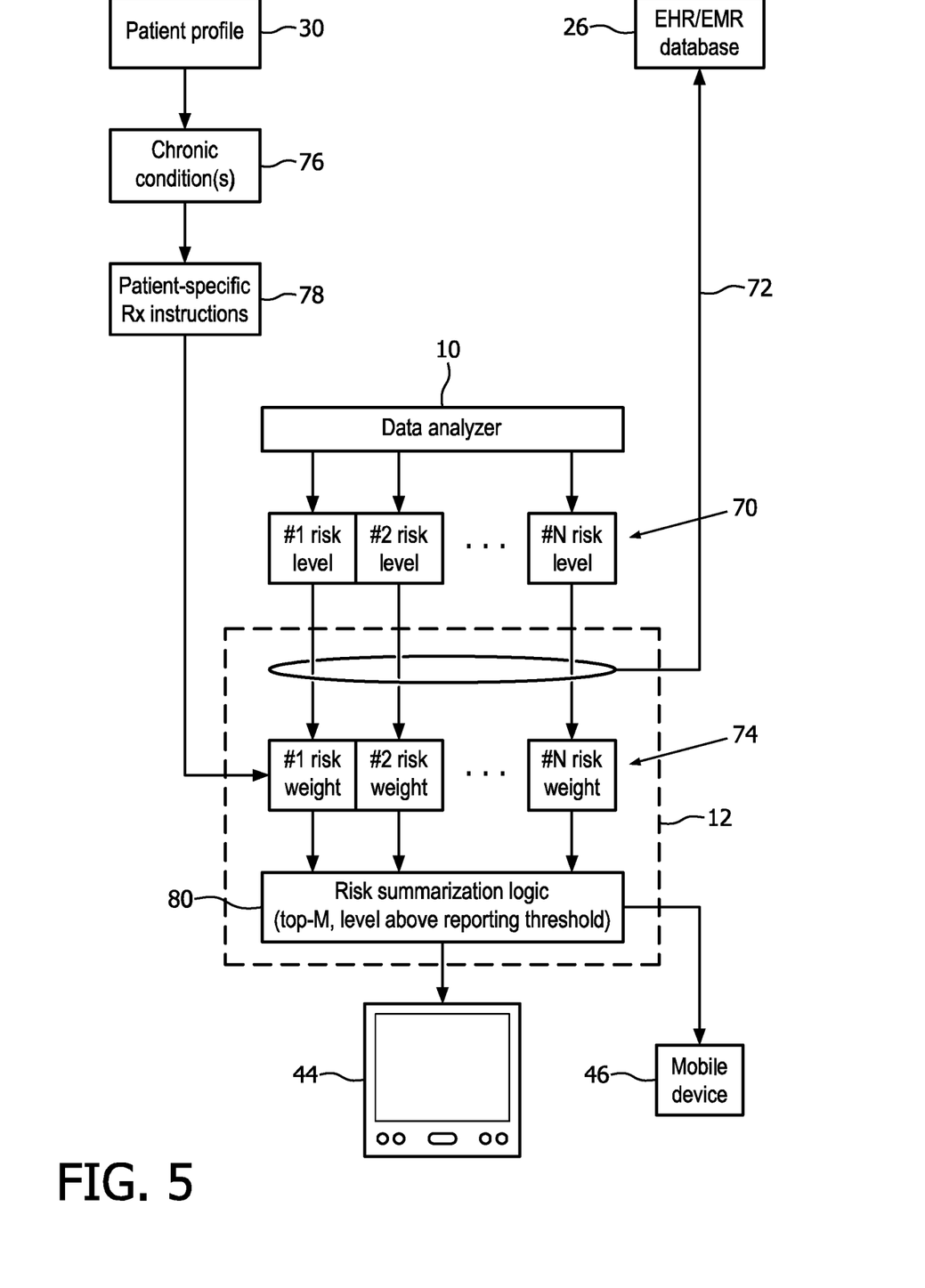
FIG. 5 diagrammatically illustrates a suitable embodiment of the risk notification component of the system of FIG. 1.

With reference to FIG. 5, an illustrative embodiment of the risk notification component 12 is described. The illustrative risk notification component 12 receives as input a set of risk levels 70. Optionally, the risk notification component 12 records these "raw" risk levels (or scores) in the EHR/EMR 26, as diagrammatically indicated in FIG. 5 by flow indicate 72. These recorded raw risk levels may then be reviewed with the patient's physician at the patient's next physical examination. For purposes of providing a rapid risk assessment in a critical care unit setting (e.g. an intensive care unit, ICU, or a cardiac care unit, CCU), the risk levels are optionally adjusted by criticality weights 74. These weights 74 may be fixed values, or may be adjusted based on patient-specific factors such as any chronic conditions 76 the patient may have (e.g. a risk of hypoxia may be enhanced by a higher weighting in the case of a patient with COPD) or any patient-specific instructions 78 provided by the patient's physician (e.g., if the patient's physician is concerned based on the physician's medical expertise about the possibility that the patient may develop sepsis, the physician may assign a higher weighting for the sepsis risk score). Risk summarization logic 80 then generates a risk assessment for the patient. For example, the risk summarization logic 80 may cause display of the top-M risk levels (where M is some integer, e.g. if M=3 then the three clinical conditions with the highest (weighted) risk level are displayed on the display device(s) 44, 46). In another example, the risk summarization logic 80 displays the risk level(s) of any clinical condition whose (weighted) risk level exceeds a reporting threshold. Use of filtering (e.g. top-M or reporting threshold) reduces the amount of information presented to medical personnel in a critical care setting by presenting only risk information for those clinical conditions for which the patient is at highest risk.

It will be appreciated that the system updates the risk levels on a real-time basis. In one approach, a table is provided which lists the input laboratory test results for each clinical condition risk inference engine $40_1, \ldots, 40_N$, and when a new test result comes in via the data collector 8 this table is consulted by the data analyzer 10 to identify which clinical conditions should be updated and the appropriate clinical condition risk inference engines are applied with the new test result. In some embodiments (not shown in FIG. 5), the risk notification component also tracks risk level over time for a clinical condition, and reports a warning if the risk level has been rising over the last two (or more) laboratory test cycles.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A system, comprising:
 a processing device programmed to perform a risk level assessment for a plurality of clinical conditions for a patient, wherein performing the risk level assessment includes:
  accessing stored laboratory test results with respective time stamps for the patient, including at least one hematology test result for the patient and at least one arterial blood gas test result for the patient; and
  for at least one clinical condition of the plurality of clinical conditions:
   training a risk inference engine by machine learning using a training set of labeled patient examples, wherein the risk inference engine comprises a neural network, a logistic regression model or a parameterized inference algorithm, wherein the labeled patient examples comprise: positive examples of patients and negative examples of patients, and wherein the positive examples are labeled as having the at least one clinical condition and the negative examples are labeled as not having the at least one clinical condition;
   determining a risk level for the clinical condition for the patient based on a clinical condition-specific sub-set of the laboratory test results using the trained risk inference engine, conditional on the clinical condition-specific sub-set of the laboratory test results being sufficient to determine the risk level using the trained risk inference engine trained;
   defining time windows around the time stamps of the laboratory test results of the clinical condition-specific sub-set of the laboratory test results, wherein the time windows are timeframes over which the laboratory test results may be relied on, respectively;
   assigning a time stamp to the determined risk level for the clinical condition for the patient as a time stamp in an intersection of the defined time windows; and
   causing a display device to display the determined risk level and the assigned time stamp for the at least one clinical condition when the determined risk level satisfies a display criterion.

2. The system of claim 1, wherein performing the risk level assessment further includes, for the at least one clinical condition:
 determining whether the clinical condition-specific sub-set of the laboratory test results is sufficient to determine the risk level based at least on availability of the laboratory test results of the clinical condition-specific sub-set of the laboratory test results; and
 conditional on the clinical condition-specific sub-set of the laboratory test results not being sufficient to determine the risk level, causing the display device to display a recommendation to order one or more laboratory tests to update the clinical condition-specific sub-set of the laboratory test results to be sufficient to determine the risk level.

3. The system of claim 2, wherein whether the clinical condition-specific sub-set of the laboratory test results is sufficient is further based on whether available laboratory test results of the clinical condition-specific sub-set of the laboratory test results are stale as indicated by time stamps of the available laboratory test results.

4. The system of claim 1, wherein performing the risk level assessment further includes:
 collecting a set of patient data including at least age and sex; and
 determining the risk level for the at least one clinical condition further based on patient data retrieved from the set of patient data.

5. The system of claim 1, wherein performing the risk level assessment further includes, for the at least one clinical condition:
 repeating the determining of the risk level and the assignment of the time stamp for the at least one clinical condition in response to an updating of a laboratory test result of the clinical condition-specific sub-set of the laboratory test results.

6. The system of claim 1, further comprising:
assigning the time stamp to the determined risk level as the oldest time stamp of the time stamps for the laboratory test results of the clinical condition-specific sub-set of the laboratory test results.

7. The system of claim 1, further comprising:
collecting laboratory test results from laboratories via an electronic network.

8. The system of claim 1, wherein said display device comprises at least one of a patient monitor and a wireless mobile device.

9. A non-transitory storage medium storing instructions readable and executable by an electronic data processing device to perform a risk level assessment for a clinical condition for a patient, wherein the non-transitory storage medium stores:
instructions for training a risk inference engine by machine learning using a training set of labeled patient examples, wherein the risk inference engine comprises a neural network, a logistic regression model or a parameterized inference algorithm, wherein the labeled patient examples comprise positive examples of patients and negative examples of patients, and wherein the positive examples are labeled as having the at least one clinical condition and the negative examples are labeled as not having the at least one clinical condition;
instructions for determining whether sufficient laboratory test results for the patient are stored in a laboratory test results data structure to perform the risk level assessment for the clinical condition for the patient using the trained risk inference engine;
instructions for, after sufficient laboratory-test results are available, determining a risk level for the clinical condition for the patient based on a clinical condition-specific sub-set of the laboratory test results using the trained risk inference engine;
instructions for defining time windows around time stamps of the laboratory test results of the clinical condition-specific sub-set of the laboratory test results, wherein the time windows are timeframes over which the laboratory test results may be relied on; respectively;
instructions for assigning a time stamp to the determined risk level for the clinical condition for the patient as a time stamp in an intersection of the defined time windows; and
instructions for causing a display device to display the determined risk level of the clinical condition in a case where the determined risk level satisfies a display criterion, and to display the assigned time stamp for the displayed risk level.

10. The non-transitory storage medium of claim 9, wherein the non-transitory storage medium further stores:
instructions for causing the display device to display a recommendation to acquire one or more laboratory test results to provide sufficient laboratory test results stored in the laboratory test results data structure to perform risk level assessment for the clinical condition.

11. The non-transitory storage medium of claim 9, wherein the non-transitory storage medium further stores:
instructions for determining availability of test results used in performing the risk level assessment; and
instructions for determining whether available test results used in performing the risk level assessment are stale based on time stamps of the available test results.

12. The non-transitory storage medium of claim 9, wherein the non-transitory storage medium further stores:
instructions for updating the risk level determination in response to an updating of a laboratory test result of the clinical condition-specific sub-set of the laboratory test results in the laboratory test results data structure.

13. The non-transitory storage medium of claim 9, wherein the non-transitory storage medium further stores:
instructions for assigning the time stamp to the determined risk level as the oldest time stamp of the clinical condition-specific sub-set of the laboratory test results.

14. The non-transitory storage medium of claim 9, wherein the non-transitory storage medium further stores:
instructions for receiving laboratory test results for the patient including at least one hematology test result and storing the received laboratory test results in the laboratory test results data structure.

15. A system, comprising:
the non-transitory storage medium of claim 11; and
a computer operatively connected to read and execute the instructions stored on the non-transitory storage medium to perform the risk level assessment for the clinical condition.

16. A method, comprising:
accessing stored laboratory test results for a patient, including at least one hematology test result for the patient and at least one arterial blood gas test result for the patient;
training a risk inference engine by machine learning using a training set of labeled patient examples, wherein the risk interference engine comprises a neural network, a logistic regression model or a parameterized inference algorithm, wherein the labeled patient examples comprise positive examples of patients and negative examples of patients, and wherein the positive examples are labeled as having, the at least one clinical condition and the negative examples are labeled as not having the at least one condition;
determining a risk level for a clinical condition for the patient based on a clinical condition-specific sub-set of the laboratory test results using the trained risk inference engine;
defining time windows around time stamps of the laboratory test results of the clinical condition-specific sub-set of the laboratory test results, wherein the time windows are timeframes over which the laboratory test results may be relied on, respectively;
assigning a time stamp to the determined risk level for the clinical condition for the patient as a time stamp in an intersection of the defined time windows; and
displaying, on a display device, the determined risk level and the assigned time stamp.

17. The method of claim 16, further comprising:
performing a hematology test for the patient by a hematology laboratory, and in response thereto supplying the at least one hematology test result for the patient; and
performing an arterial blood gas test for the patient by an arterial blood gas laboratory, and in response thereto supplying the at least one arterial blood gas test result for the patient.

18. The method of claim 17, further comprising performing a histopathology test for the patient by a histopathology laboratory, and in response thereto supplying a histopathology test result for the patient.

19. The system of claim 1, further comprising:
a hematology laboratory configured to perform a hematology test for the patient and in response thereto to supply to the processing device the at least one hematology test result for the patient; and
an arterial blood gas laboratory configured to perform an arterial blood gas test for the patient and in response thereto to supply to the processing device the at least one arterial blood gas test result for the patient.

20. The system of claim 19, further comprising a histopathology laboratory configured to perform a histopathology test for the patient and in response thereto to supply to the processing device a histopathology test result for the patient.

* * * * *